United States Patent [19]

Hathman

[11] Patent Number: 5,702,356
[45] Date of Patent: Dec. 30, 1997

[54] DISPOSABLE WOUND DRESSING PERMITTING NON-INVASIVE EXAMINATION

[76] Inventor: Johnnie L. Hathman, 5020 Shenandoah Ave., Los Angeles, Calif. 90056

[21] Appl. No.: 648,024
[22] PCT Filed: Dec. 23, 1993
[86] PCT No.: PCT/US93/12577
   § 371 Date: May 17, 1996
   § 102(e) Date: May 17, 1996
[87] PCT Pub. No.: WO95/17146
   PCT Pub. Date: Jun. 29, 1995
[51] Int. Cl.⁶ ............................................. A61F 5/00
[52] U.S. Cl. ................... 602/41; 602/42; 602/54; 602/79; 128/888
[58] Field of Search ............ 602/41–59; 128/888, 128/889; 604/180

[56] References Cited

U.S. PATENT DOCUMENTS

| | | | |
|---|---|---|---|
| 4,399,816 | 8/1983 | Spangler | 602/42 |
| 4,641,643 | 2/1987 | Greer | 602/42 |
| 4,909,243 | 3/1990 | Frank et al. | 602/42 |
| 4,917,112 | 4/1990 | Kalt | 602/42 |
| 5,086,763 | 2/1992 | Hathman | 602/42 |
| 5,106,362 | 4/1992 | Gilman | 602/47 |
| 5,449,340 | 9/1995 | Tollini | 604/180 |

Primary Examiner—Richard J. Apley
Assistant Examiner—Kim M. Lee
Attorney, Agent, or Firm—Paul H. Ware

[57] ABSTRACT

A dressing for wounds that permits a cover member to be repeatedly unsealed or opened for inspection, medication of the wound or for any other purpose and then repeatedly resealed without loss of integrity of the seal. Opening and resealing may be accomplished by means of a hasp comprising a latch and an eye or the like. The dressing may be secured to the body skin of a user by means of an epidermal adhesive tape strip base member that has a wound circumscribing aperture. A pad, medicated or not, may be supplied to cover a wound under treatment within the circumscription of said circumscribing aperture.

8 Claims, 6 Drawing Sheets

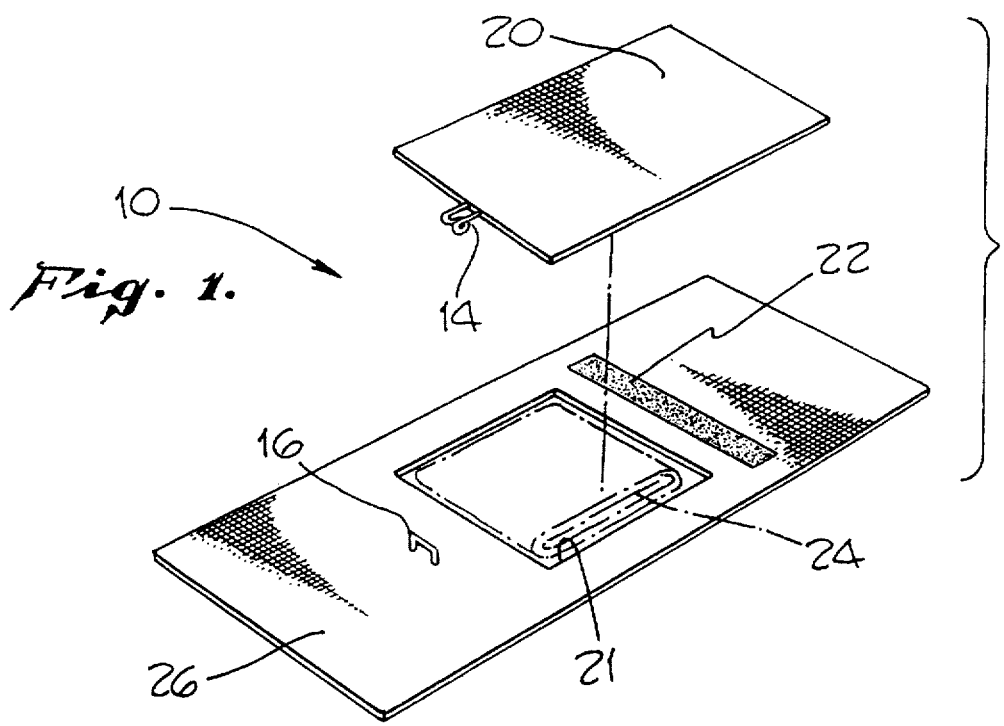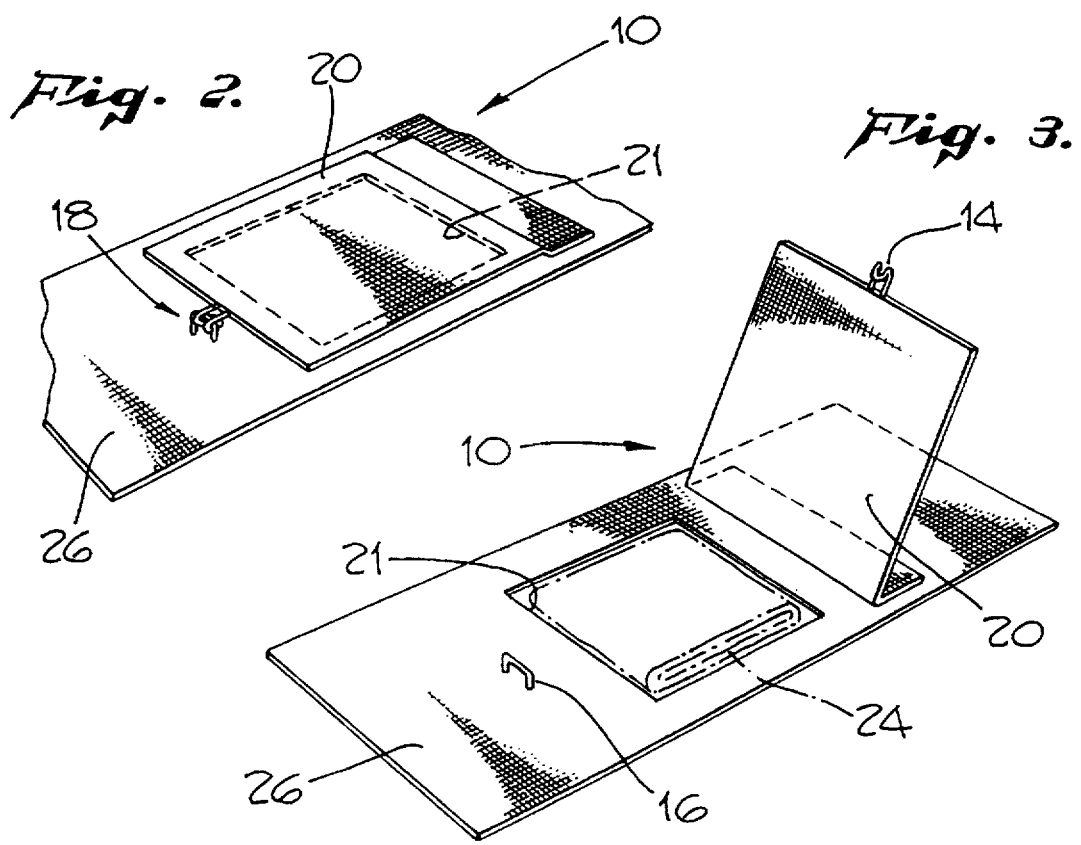

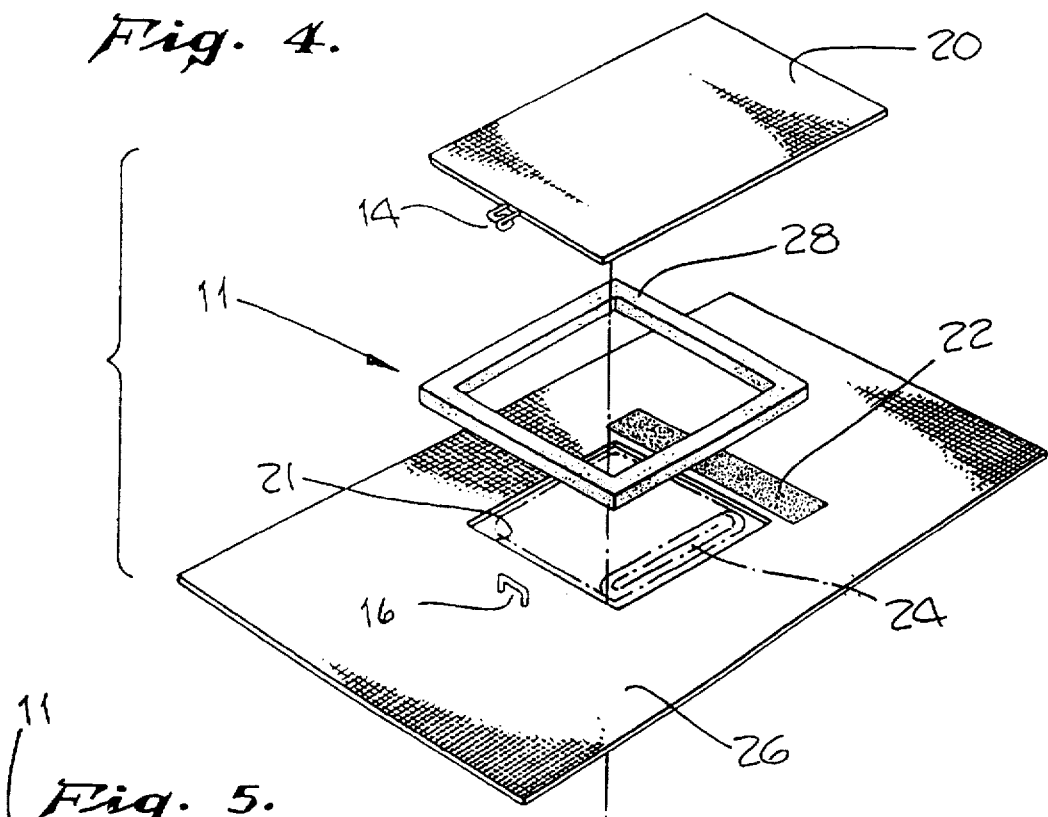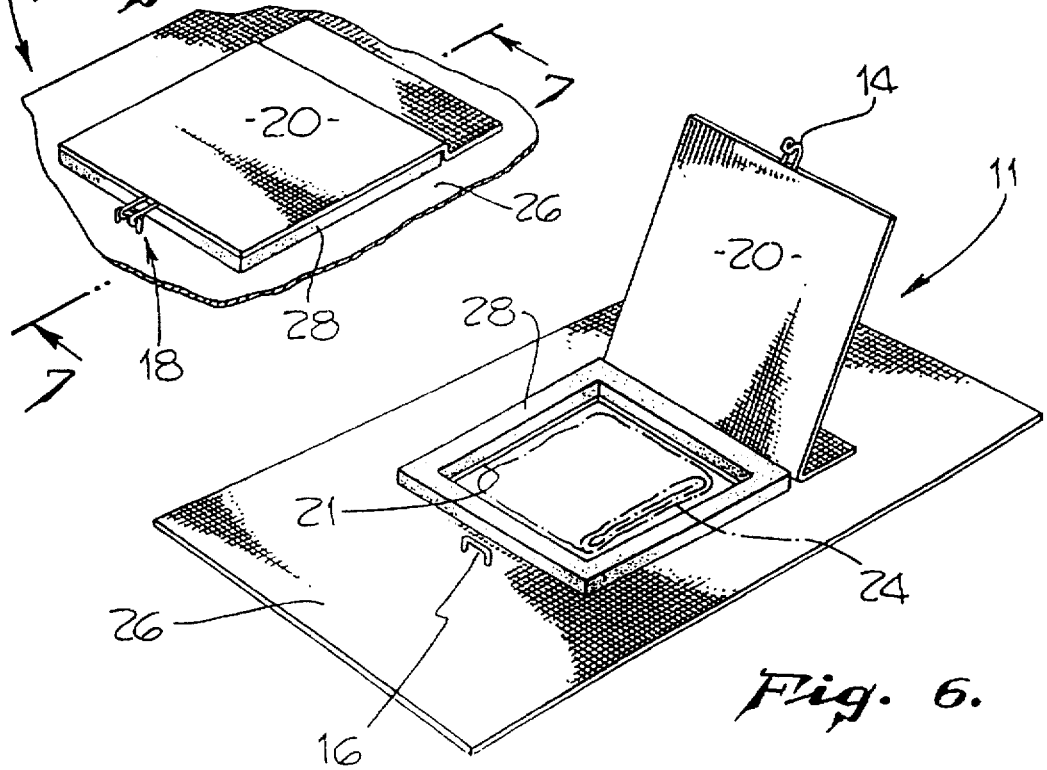

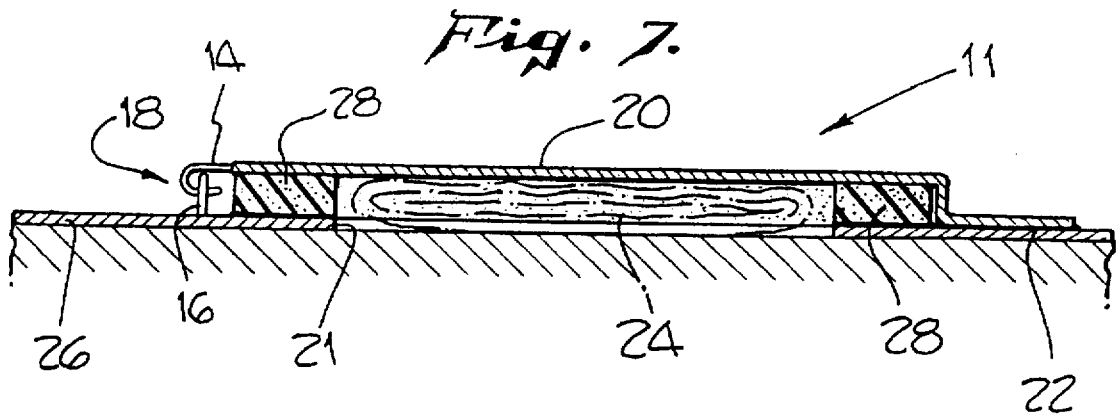
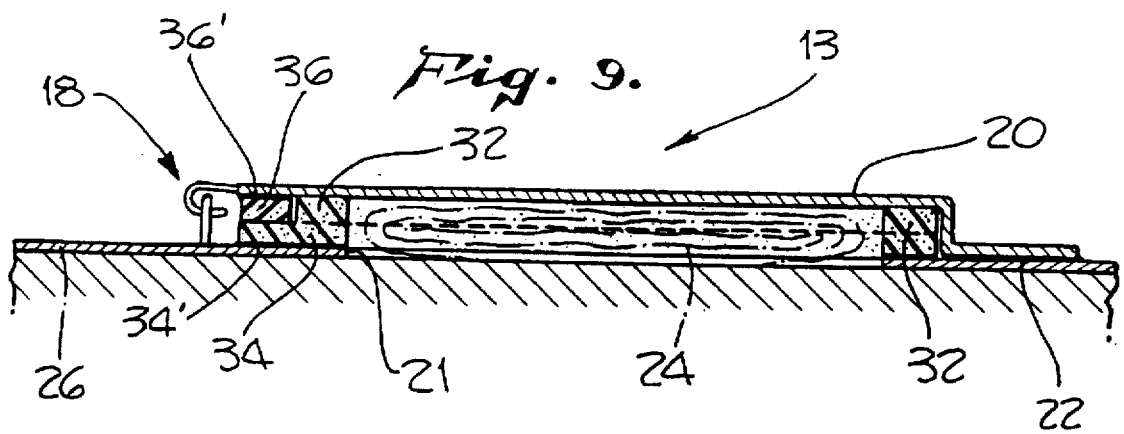
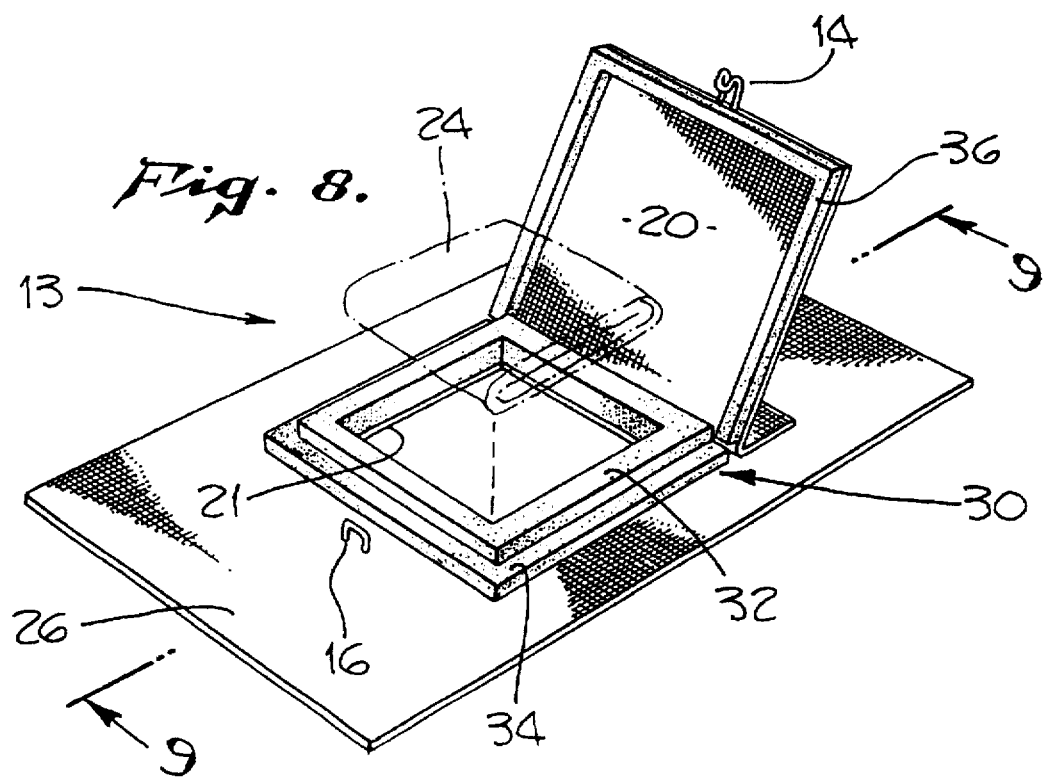

DISPOSABLE WOUND DRESSING PERMITTING NON-INVASIVE EXAMINATION

TECHNICAL FIELD

This invention relates to disposable bandages and surgical dressings for wounds and particularly to those wound dressings that may be employed in connection with recurrent observation, examination and repeated medication of wounds.

In the employment of the novel wound dressing described in this specification, it is intended that the wound under treatment be completely circumscribed by an opening in the dressing. As will become apparent, means are provided whereby the wound may be inspected and treated with medication without removal of the primary body of the dressing itself.

BACKGROUND ART

The prior art includes U.S. Pat. No. 3,026,874, issued Mar. 27, 1962 to R. C. Stevens for WOUND SHIELD. The device provides controlled drainage for a wound and is characterized as easily sterilizable thus leading to the inference of non-disposability.

Another prior art device is described in the U.S. Pat. No. 4,470,410, granted to E. M. Elliot for PROTECTIVE RETAINING DEVICE AND METHOD, issued Sep. 11, 1984. The device described appears to be comparatively expensive and complicated to manufacture. It appears to have as its primary purpose the protection of the site of an intravenous catheter.

Yet another prior art device has been illustrated in the U.S. Pat. No. 3,888,247, granted to C. B. Stenvall for FIRST AID BANDAGE issued Jun. 10, 1975. The innovative device described in that patent provides that a lightly adhered breathable surgical tape that is first placed over the wound shall be left in contact therewith until after healing has been accomplished.

The patent entitled PROTECTIVE DEVICE by inventors Kohn et al bearing U.S. Pat. No. 4,709,695 was issued on Dec. 1, 1987, and contemplates a contrivance expected to be prepared by cutting to size for each application.

These prior art devices are commendable and show a truly creative spirit for their times and intended applications. The inventors and their inventions have contributed remarkably to the technology involved. However, these prior art structures do not include those combined elements of the invention described and submitted herewith that provide greater facility of use and ingenious arrangement of components that make the instant invention the high culmination in the art of disposable wound dressings that permit repeated, non-wound disturbing observations and recurring medications of a wound undergoing the healing process.

DISCLOSURE OF INVENTION

In accordance with the instant invention, there is provided a disposable, inexpensive and easy to use wound dressing that expedites repetitious examination, observation and medication of a wound such as an injury resulting, in general, from a bruise, cut, laceration or the like. The inventive wound dressing contemplated by the device described envisions in succession, the initial sealing of a bandage covering and protecting the wound involved, the uninvasive unsealing of the bandage in such manner as to allow inspection of the wound under healing, observation of the wound, medication thereof as may be required, and the resealing of said bandage to again cover and protect the wound without loss of integrity of the sealing properties of the dressing.

BRIEF DESCRIPTION OF DRAWINGS

Further advantages and features of the instant invention will be more fully apparent to those skilled in the art to which the invention pertains from the ensuing detailed description thereof, regarded in conjunction with the accompanying drawings wherein like reference numerals refer to like parts throughout and in which:

FIG. 1 is an exploded, perspective view of a first, simple embodiment of the Disposable Wound Dressing Permitting Non-Invasive Examination.

FIG. 2 is a perspective view of the embodiment of FIG. 1 showing the dressing closed and latched.

FIG. 3 is another perspective view of the embodiment of FIG. 1 showing a medication pad in place and the dressing opened for inspection or the like.

FIG. 4 is an exploded perspective view of a second embodiment of the Disposable Wound Dressing Permitting Non-Invasive Examination and having a standoff member, the service of which will become apparent in the following discourse.

FIG. 5 is a detail perspective view showing the closure and latching of the embodiment of FIG. 4 so as to effectuate the seal thereof.

FIG. 6 is an open, perspective view of the embodiment of FIG. 4 showing how it might be unsealed for inspection and possible replacement of a medication pad.

FIG. 7 is an enlarged, detail cross sectional view of the embodiment of FIG. 4 taken along the sight lines 7—7 of FIG. 5.

FIG. 8 is yet another embodiment, a third, of the Disposable Wound Dressing Permitting Non-Invasive Examination showing a unique stepped standoff member whose utility will be made apparent in the ensuing discourse.

FIG. 9 is an enlarged, detail cross sectional view of the embodiment of FIG. 8 taken along the sight lines 9—9 of FIG. 8 with the circumscribing cover member closed and latched so as to effect a seal.

BEST MODE FOR CARRYING OUT THE INVENTION

Figure 10:
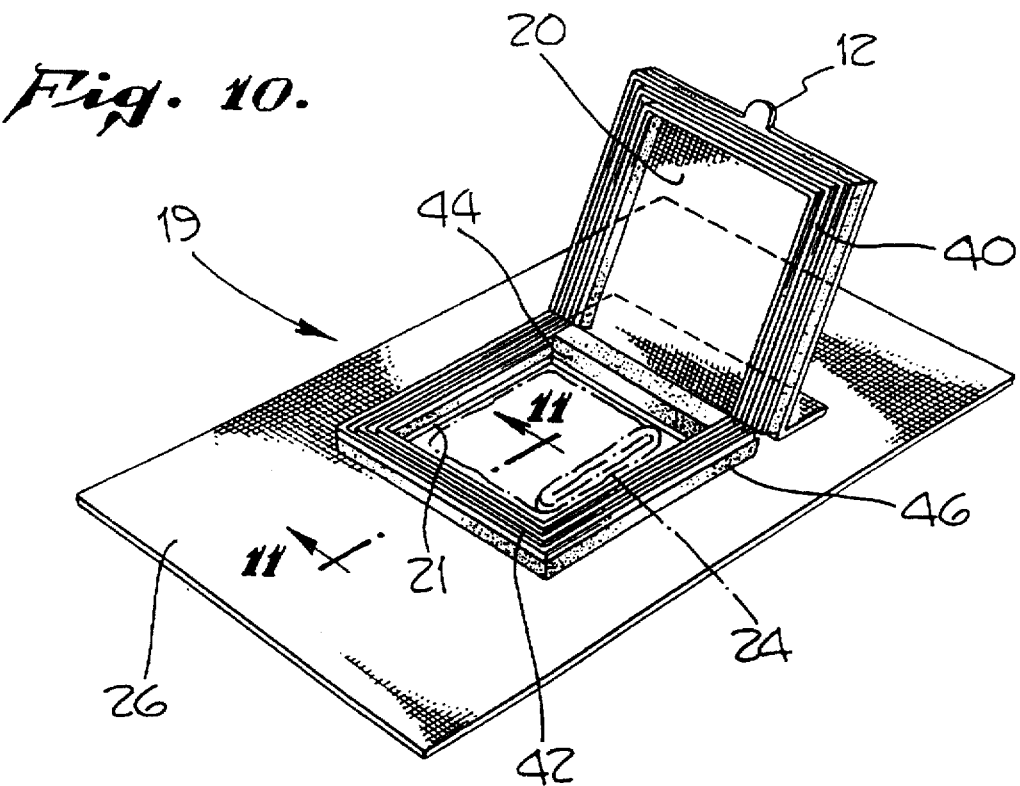
FIG. 10 is a perspective view of a fourth embodiment of the Disposable Wound Dressing Permitting Non-Invasive Examination having a tongue-and-groove latching mechanism.

Referring to the drawings and to FIGS. 1 through 3 with greater particularity, the Disposable Wound Dressing Permitting Non-Invasive Examination is denoted generally by the numeral 10. FIG. 1 shows the sealing cover member 20 prior to its secure attachment to adhesive strip 22 so as to form a hinge at one end of said sealing cover operative when opening or closing the dressing. An epidermal adhesive tape strip base member 26 adheres the wound dressing to the body skin of the patient and is so placed that the wound is circumscribed by the wound circumscribing aperture 21. An optional, replaceable pad which may be medicated or not as desired, is denoted by the numeral 24, and may be placed over the wound under treatment and within circumscribing aperture 21, however, medication may be applied or not by any other means desired and the illustration showing the pad 24 is not to be considered a limitation on the generality of the device. A hasp mechanism 18, FIG. 2, having a latch and eye denoted respectively by numerals 14 and 16, effectuates positive closing and sealing of the dressing.

FIG. 2 shows the sealing cover member 20 closed subsequent to its secure attachment at adhesive strip 22 and with latch and eye mechanism, respectively 14 and 16, engaged to form hasp 18 thus securing the sealing cover member 20 over wound circumscribing aperture 21 so as to protect the wound and secure the position of any medication applied.

FIG. 3 displays the assembled device opened after application and illustrates the hinge action constraining sealing cover member 20 by means of the adhesive strip 22. The wound dressing may be opened, as illustrated, so as to inspect the wound under healing process, to apply medication to the wound or for any other purpose desired and then, after the accomplishment of the purpose for which the dressing was opened, resealed without loss of integrity of the original seal.

Directing attention now to FIGS. 4 through 7, a second embodiment, denoted generally by the numeral 11, of the Disposable Wound Dressing Permitting Non-Invasive Examination may be examined. FIG. 4 is an exploded perspective view showing the constituent parts thereof prior to assembly. A sealing cover 20 is shown as to be attached by means of adhesive strip 22 to the epidermal adhesive tape base member 26. The cover 20 has a latch 14 intended for engagement with eye 16 on epidermal adhesive tape member 26. A medication pad 24 is shown in place upon a wound being treated; the wound has not been shown. Interposed between sealing cover 20 and epidermal adhesive tape base member 26 and dimensioned and positioned so as to be in registry with circumscribing aperture 21 in tape member 26, there is a standoff member 28. One of the purposes served by standoff member 28 is the alleviation of pressure upon a wound where such is necessary or desired in the treatment thereof.

FIG. 5 illustrates the configuration of the dressing when closed by means of sealing cover 20 over standoff member 28 and secured by hasp 18. The integrity of the seal is intended to be maintained by means of sealing cover 20 as secured hingedly and adhesively by means of adhesive strip 26 and standoff member 28 acting cooperatively with hasp mechanism 18.

FIG. 6 depicts the dressing opened subsequent to application to permit observation, medication or for any other purpose desired. Sealing cover 20 is shown in its hinge-open position while standoff member 28 is shown in registry with circumscribing aperture 21 in epidermal adhesive tape strip base member 26.

FIG. 7 represents an enlarged cross sectional view taken along the sight lines 7—7 of FIG. 5. The configuration of the sealing cover 20 with respect to the standoff member 28 may be more clearly understood in this enlarged view as may be the registration of standoff member 28 with circumscribing aperture 21. An additional point of view is also provided for explicating the cooperation of latch 14 with eye 16 to form hasp 18.

A third embodiment of the Disposable Wound Dressing Permitting Non-Invasive Examination is represented in FIGS. 8 and 9 and denoted generally by the numeral 13. FIG. 8 shows the dressing as applied after assembly and opened for inspection or for other purposes. The sealing cover 20 has a top circumscribing member 36 that acts in cooperation with a stepped standoff member 30 in effectuating a positive seal and a pressure reducing protection of a wound under treatment. Close examination reveals that top circumscribing member 36 is of the proper dimension and configuration so as to fit about a first stepped member 32 and onto and in abutment registration with a second stepped member 34.

FIG. 9 represents an enlarged cross sectional view of this third embodiment taken along the sight lines 9—9 of FIG. 8. Detail there shows the adhesive attachment of stepped standoff member 30 to epidermal adhesive tape member 26 at second stepped member 34 by means of adhesive 34' and the adhesive attachment of top circumscribing member 36 to sealing cover 20 by means of adhesive 36'. FIG. 9, of course, shows the dressing sealed and latched by means of hasp 18.

Figure 11:
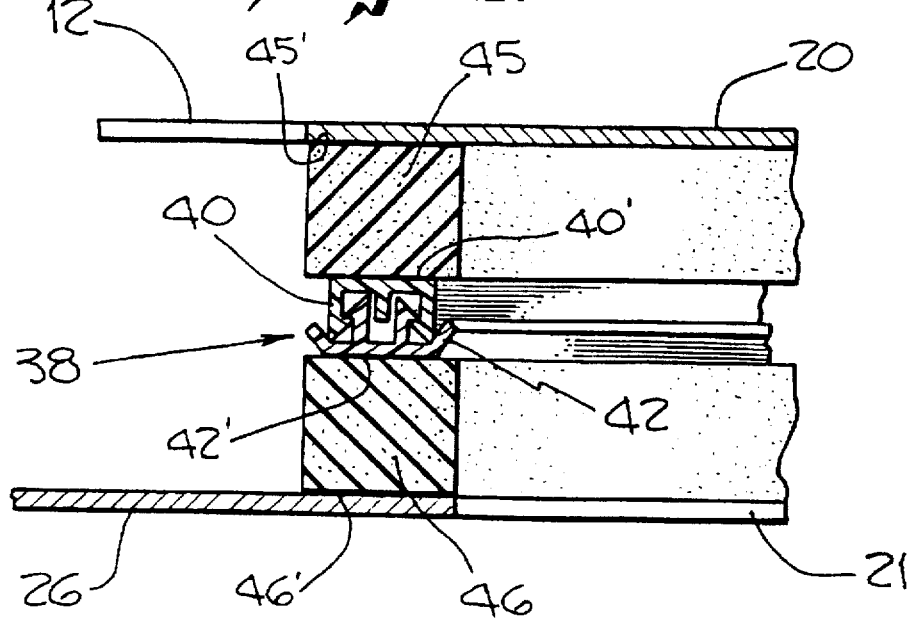
FIG. 11 is an enlarged detail cross sectional view taken along the sight lines 11—11 of FIG. 10 with the circumscribing cover member closed so as to effect a seal.

An additional embodiment, the fourth, is depicted in FIGS. 10 and 11 in which the Disposable Wound Dressing Permitting Non-Invasive Examination is denoted generally by the numeral 19. A tongue-and-groove latching mechanism 38 is comprised of an upper latching member 40 which cooperates with a lower latching member 42 to bring about a seal of exceptionally high integrity. Sealing cover 20 supports the upper latching member 40 which is adhered to a top support member 45 by means of adhesive 40' which top support member 45 is in turn adhered to sealing cover 20 by adhesive 45'. In like manner, epidermal adhesive tape 26 supports the lower latching member 42 which is adhered to a bottom support member 46 by means of adhesive 42' which bottom support member 46 is in turn adhered to epidermal adhesive tape member 26 by means of adhesive 46'. A rear standoff member 44 is provided to enhance the structure and integrity of the seal effected by the cooperating members. A tab 12 is also provided in order to facilitate opening and closing the sealing cover 20 to provide access to the wound under treatment.

Figure 12:
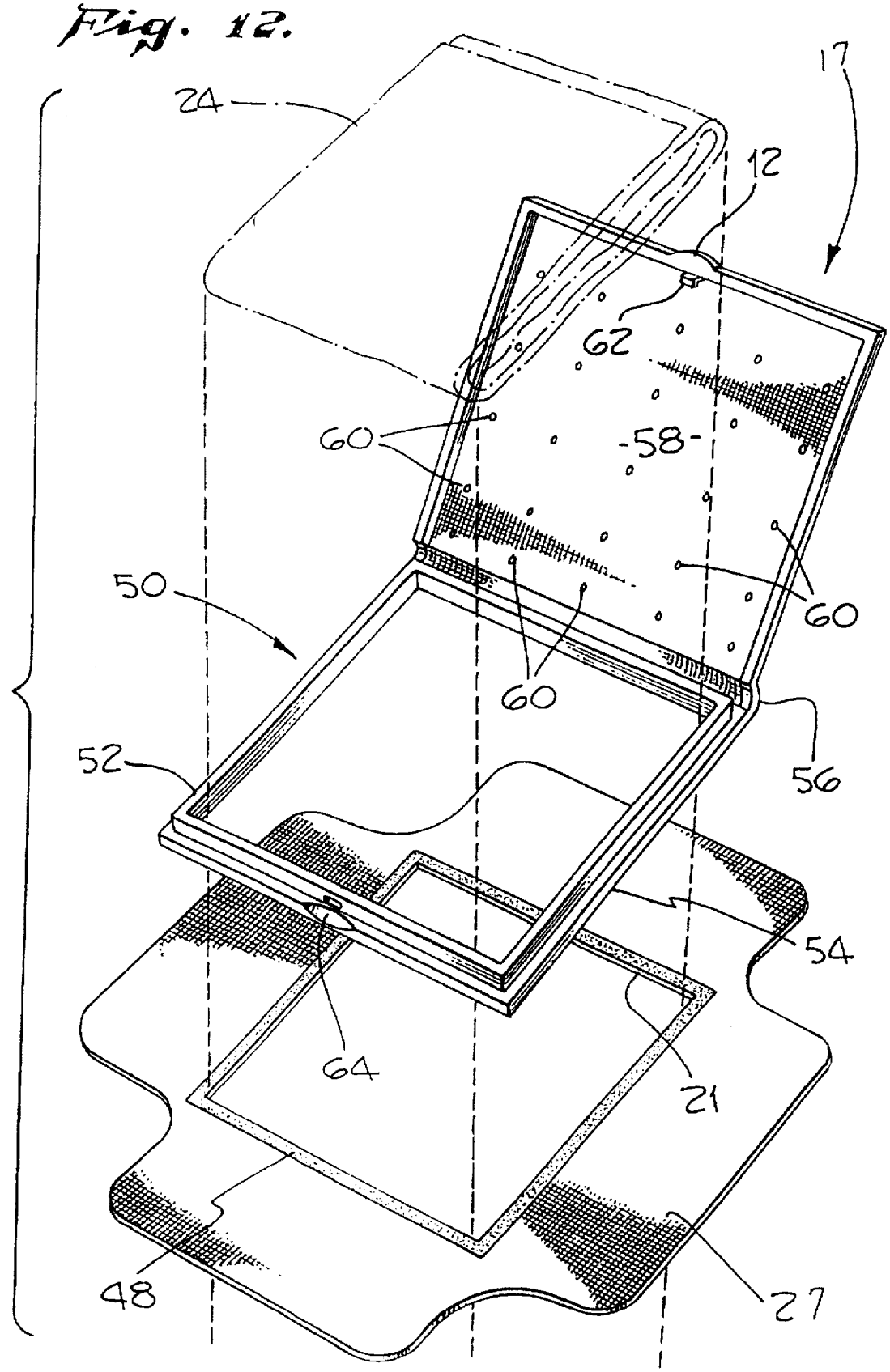
FIG. 12 is an exploded view of a fifth embodiment of the Disposable Wound Dressing Permitting Non-Invasive Examination showing a contourable epidermal adhesive tape member and additional advantages that will become apparent in the ensuing discourse.

A fifth embodiment of the Disposable Wound Dressing Permitting Non-Invasive Examination is portrayed in exploded view in FIG. 12 and denoted generally by the numeral 17. This embodiment features a contourable epidermal adhesive tape base member 27 that has an adhesive pattern 48 thereupon for the affixation of an adhered standoff member 50. Adhered standoff member 50 comprises a lower member 54 adapted to be adhered to adhesive pattern 48 and in registry with circumscribing aperture 21 in epidermal adhesive member 27 and an upper member 52 intended to be covered by attached covering member 58. Attached covering member 58 connects with standoff member 50 through resilient hinge 56. Covering member 58 includes venting apertures 60 whose purpose is to provide circulation of ambient air to a wound under treatment. The instant embodiment provides a tab 12 and a latching mechanism comprising a latching member 62 adapted to be received into a latch recess 64 so as to effect positive closure of the covering member 58. Contourable epidermal adhesive base tape member 27 permits adherence of the dressing to irregularly shaped parts of the body and the forming around curved portions thereof of the dressing.

Figure 13:
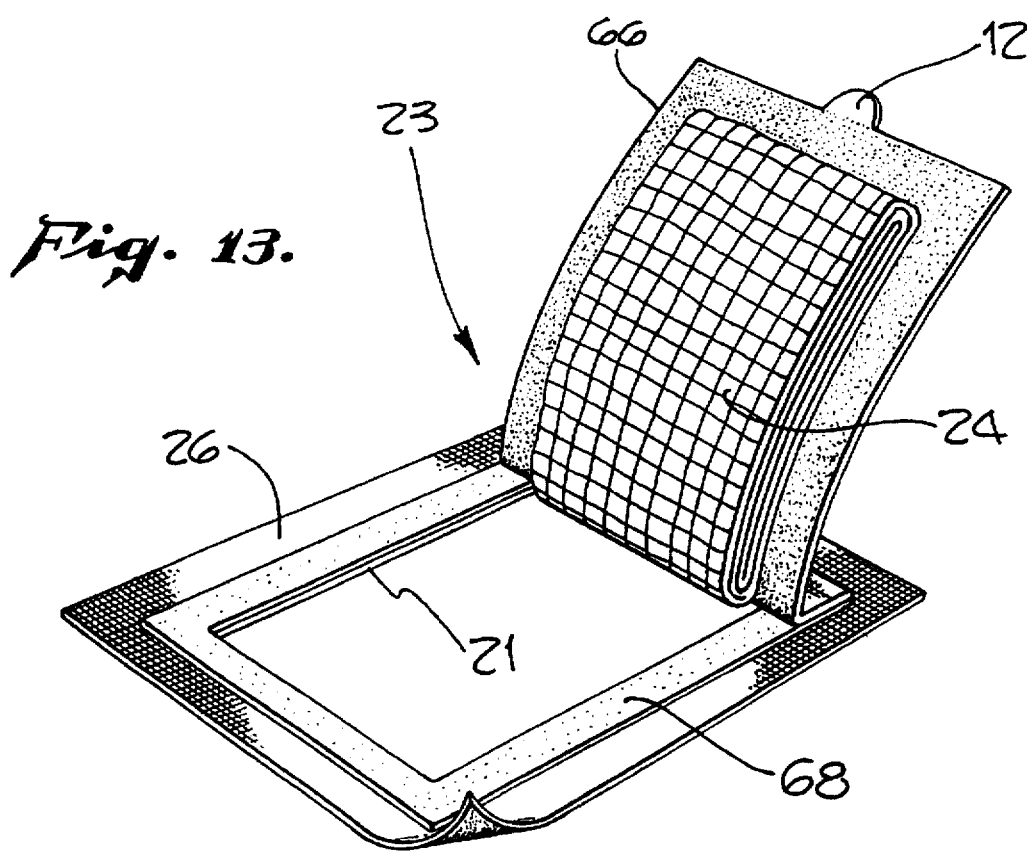
FIG. 13 is a perspective open view of a sixth embodiment of the Disposable Wound Dressing Permitting Non-Invasive Examination having unique characteristics to be explored in the following exposition.
Figure 14:
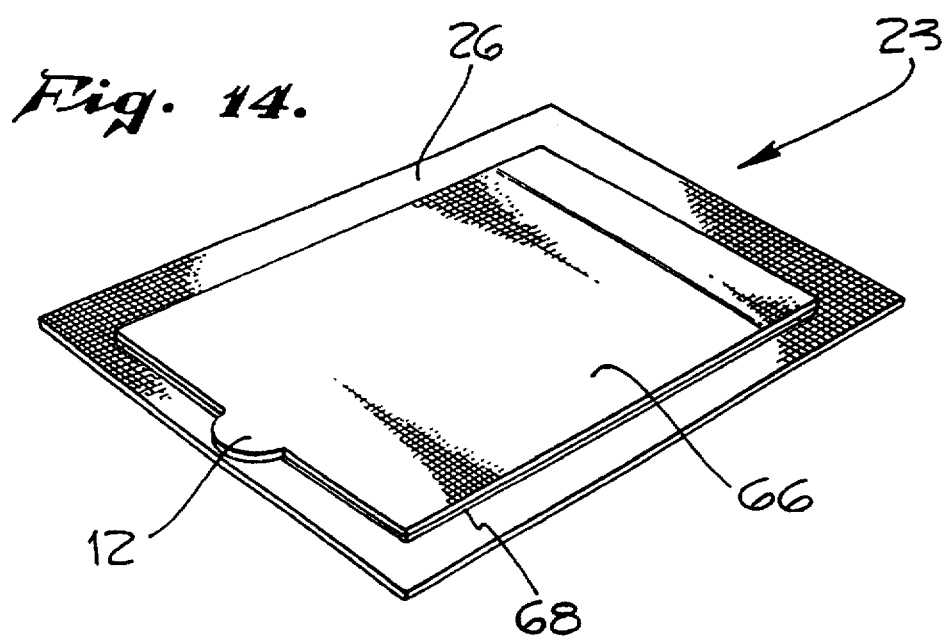
FIG. 14 is a perspective view of the embodiment of FIG. 13 shown in a closed and sealed position.

FIGS. 13 and 14 depict a sixth embodiment of the Disposable Wound Dressing Permitting Non-Invasive Examination denoted in general by the numeral 23. The circumscribing aperture 21, intended to circumscribe the wound under treatment, is situated in the epidermal adhesive tape strip base member 26. An adhesive backed sealing cover member 66 carries a pad 24 which may be medicated if desired, adhered to its wound facing surface. An adhesive cover matching strip 68 carried on the epidermal adhesive tape member 26 accomplishes positive sealing of the bandage when closed. A tab 12 is provided to facilitate opening and closing the cover 66.

I claim:

1. A disposable wound dressing permitting non-invasive examination of and access to a wound under treatment, comprising;

an epidermal adhesive tape strip base member for adhering the dressing to the skin of a user of the dressing, said epidermal adhesive tape strip base member having a wound circumscribing aperture;

a sealing cover member;

a stepped standoff member adhesively secured to said epidermal adhesive tape strip base member and in circumscribing registry with said wound circumscribing member and interposed between said epidermal adhesive tape strip base member and said sealing cover member, said stepped standoff member comprising:

a first stepped member; and a second stepped member;

a top circumscribing member adhesively secured to said sealing cover member and so disposed as to fit about said first stepped member of said stepped standoff member and in abutment registry with said second stepped member of said stepped standoff member;

means for securing said sealing cover member at one end to said epidermal adhesive tape strip base member; and means for sealably closing said sealing cover member to said epidermal adhesive tape strip base member so as to maintain and secure said top circumscribing member about said first stepped member of said stepped standoff member and in abutment registry with said second stepped member of said stepped standoff member and so as to cover said wound circumscribing aperture.

2. The disposable wound dressing of claim 1 and including a replaceable pad placed over the wound under treatment and within said wound circumscribing aperture.

3. The disposable wound dressing of claim 1 in which said means for securing said sealing cover member at one end to said epidermal adhesive tape strip base member is an adhesive strip.

4. The disposable wound dressing of claim 1 in which said means for sealably closing said sealing cover member to said epidermal adhesive tape strip base member so as to maintain and secure said top circumscribing member about said first stepped member of said stepped standoff member and in abutment registry with said second stepped member of said stepped standoff member and so as to cover said wound circumscribing aperture is a hasp.

5. The disposable wound dressing of claim 1 in which said hasp comprises:

a latch formed on said sealing cover member, and an eye formed on said epidermal adhesive tape strip base member and wherein said latch is adapted to be inserted into said eye to form a sealing closure of said sealing cover member to said epidermal adhesive tape strip base member and over said wound circumscribing aperture.

6. A disposable wound dressing permitting non-invasive examination of and access to a wound under treatment, comprising:

an epidermal adhesive tape strip base member for adhering the dressing to the skin of a user of the dressing, said epidermal adhesive tape strip base member having a wound circumscribing aperture;

a sealing cover member;

a tongue and groove latching mechanism comprising:

an upper latching member secured to said sealing cover member; and a lower latching member secured to said epidermal adhesive tape strip base member;

a rear standoff member disposed at one end of said circumscribing aperture and adhesively secured to said epidermal adhesive tape strip base member;

means for securing said sealing cover member at one end to said epidermal adhesive tape strip base member;

means for gasping and sealably closing said upper latching member secured to said sealing cover member to said lower latching member secured to said epidermal adhesive tape strip base member so as to cover said wound circumscribing aperture;

wherein said upper latching member is secured to said sealing cover member by means of a top support member, said top support member being adhesively secured both to said sealing cover member and to said upper latching member of said tongue and groove latching mechanism; and wherein said lower latching member is secured to said epidermal adhesive tape strip base member by means of a bottom support member, said bottom support member being adhesively secured both to said epidermal adhesive tape strip base member and to said lower latching member of said tongue and groove latching mechanism.

7. A disposable wound dressing permitting non-invasive examination of and access to a wound under treatment, comprising:

a contourable epidermal adhesive tape strip base member for adhering the dressing to the skin of a user of the dressing, said epidermal adhesive tape strip base member having a wound circumscribing aperture;

an adhesive pattern about said wound circumscribing aperture;

an adhered standoff member adapted to be adhesively secured at said adhesive pattern and about said wound circumscribing aperture, said adhered standoff member comprising;

an upper adhered standoff member; formed upon a lower adhered standoff member and joined by means of a resilient hinge to an attached covering member, said attached covering member having a plurality of venting apertures formed therein and said attached covering member being adapted to fit about said upper adhered standoff member and in abutment registry with said lower adhered standoff member;

a latching member and a latching member recess formed on said adhered standoff member for effecting positive sealing closure of said attached covering member to said lower adhered standoff member so as to cover and seal said wound circumscribing aperture; and means for grasping said attached covering member so as to effect opening and closing of said attached covering member.

8. The disposable wound dressing of claim 7 and including a replaceable pad placed over the wound under treatment and within said wound circumscribing aperture.

* * * * *